US010238839B2

(12) United States Patent
Ehrlich (10) Patent No.: US 10,238,839 B2
(45) Date of Patent: *Mar. 26, 2019

(54) PULMONARY ARTERY HEAD CATHETER HOLDER

(71) Applicant: Kenneth Ehrlich, Borger, TX (US)

(72) Inventor: Kenneth Ehrlich, Borger, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/702,751

(22) Filed: Sep. 12, 2017

(65) Prior Publication Data

US 2017/0368311 A1    Dec. 28, 2017

Related U.S. Application Data

(63) Continuation-in-part of application No. 14/335,079, filed on Jul. 18, 2014, now Pat. No. 9,789,287.

(51) Int. Cl.
*A61M 25/02* (2006.01)
*A61B 5/0215* (2006.01)
*A61B 5/00* (2006.01)

(52) U.S. Cl.
CPC .......... *A61M 25/02* (2013.01); *A61B 5/0215* (2013.01); *A61B 5/6803* (2013.01); *A61B 5/6814* (2013.01); *A61B 5/6852* (2013.01); *A61M 2025/026* (2013.01); *A61M 2025/0206* (2013.01); *A61M 2025/0213* (2013.01); *A61M 2210/06* (2013.01)

(58) Field of Classification Search
CPC .......... A61M 2025/0206; A61M 25/02; A61M 2025/0213; A61M 2025/022; A61M 2025/0226; A61M 2025/0253; A61M 2210/06

See application file for complete search history.

(56) References Cited

U.S. PATENT DOCUMENTS

| 4,308,642 | A | * | 1/1982 | Heyman | A44B 99/00 |
| | | | | | 128/DIG. 26 |
| 5,131,412 | A | * | 7/1992 | Rankin | A61F 5/3761 |
| | | | | | 128/869 |
| 5,188,101 | A | * | 2/1993 | Tumolo | A61M 25/02 |
| | | | | | 128/101.1 |
| 7,473,816 | B2 | * | 1/2009 | Hall | A61F 13/08 |
| | | | | | 602/41 |
| 2008/0103456 | A1 | * | 5/2008 | Johnson | A61B 5/6864 |
| | | | | | 604/264 |
| 2013/0306081 | A1 | * | 11/2013 | Devapatla | A61F 5/0193 |
| | | | | | 128/876 |

\* cited by examiner

*Primary Examiner* — Bradley J Osinski
*Assistant Examiner* — Nilay J Shah
(74) *Attorney, Agent, or Firm* — Shannon L. Warren (57) ABSTRACT

A catheter holder assembly for selectively holding a portion of a one or more catheter tubes to a head of a user. Comprising head mount assembly, a one or more catheter holders, the one or more catheter tubes, a catheter. The one or more catheter holders comprise a first catheter holder. The one or more catheter holders are attached to the head mount assembly. Head mount assembly is configured to releaseably attach to the head of the user. The one or more catheter holders releaseably hold the one or more catheter tubes. The one or more catheter tubes each comprise the catheter at a first end being a downstream of the one or more catheter holders and an IV bag at a second end being an upstream of the one or more catheter holders. The catheter is configured to attach to a portion of the user at an insertion point.

10 Claims, 8 Drawing Sheets

PULMONARY ARTERY HEAD CATHETER HOLDER

CROSS-REFERENCE TO RELATED APPLICATIONS

This application claims benefit to US Patent Application Number(s) Ser. No. 14/335,079 filed on Jul. 18, 2014.

STATEMENT REGARDING FEDERALLY SPONSORED RESEARCH OR DEVELOPMENT (IF APPLICABLE)

Not applicable.

REFERENCE TO SEQUENCE LISTING, A TABLE, OR A COMPUTER PROGRAM LISTING COMPACT DISC APPENDIX (IF APPLICABLE)

Not applicable.

BACKGROUND OF THE INVENTION

None of the known inventions and patents, taken either singularly or in combination, is seen to describe the instant disclosure as claimed.

BRIEF SUMMARY OF THE INVENTION

A catheter holder assembly for selectively holding a portion of a one or more catheter tubes to a head of a user. Comprising head mount assembly 102, a one or more catheter holders, said one or more catheter tubes, a catheter. Said one or more catheter holders comprise a first catheter holder. Said one or more catheter holders are attached to said head mount assembly 102. head mount assembly 102 is configured to releaseably attach to said head of said user. Said one or more catheter holders releaseably hold said one or more catheter tubes. Said one or more catheter tubes each comprise said catheter at a first end being a downstream of said one or more catheter holders and an IV bag at a second end being an upstream of said one or more catheter holders. Said catheter is configured to attach to a portion of said user at an insertion point. Said catheter holder assembly is configured to relieve stress between said catheter and said user by supporting one or more catheter tubes 114 between said insertion point and said IV bag. Said one or more catheter holders are positioned above said insertion point. head mount assembly 102 comprises a mesh portion and a rim. Said mesh portion wraps around a portion of said head. Said mesh portion attaches around a circumference of said rim. head mount assembly 102 is configured to slide onto said head by stretching said rim around said head, and pressing a portion of said mesh portion into a vertex of said head. Said one or more catheter holders attach to a portion of said head mount assembly 102.

A method of use steps for a catheter holder assembly comprising: a first method of use step comprising attaching head mount assembly 102 to a one or more catheter holders. A second method of use step comprising releaseably attaching head mount assembly 102 to a head of a user, and. A third method of use step comprising releaseably holding a one or more catheter tubes with said one or more catheter holders. Wherein. head mount assembly 102 comprising a mesh portion and a rim. Said mesh portion is attached to a circumference of said rim. Said rim comprises a head aperture. head mount assembly 102 is configured to selectively attach to said head by stretching a portion of said rim around said head, sliding a portion of said head through said head aperture. Said rim comprises a one or more aperture diameters. Said rim comprises and elastic material. Said one or more aperture diameters vary depending on pressure applied to said rim.

BRIEF DESCRIPTION OF THE SEVERAL VIEWS OF THE DRAWING

FIG. 1 illustrates a perspective overview view of a catheter holder assembly 100a.

FIG. 5A illustrates an elevated bottom side view of a catheter holder assembly 100a.

FIG. 5B illustrates an elevated first side view of a catheter holder assembly 100a.

DETAILED DESCRIPTION OF THE INVENTION

The following description is presented to enable any person skilled in the art to make and use the invention as claimed and is provided in the context of the particular examples discussed below, variations of which will be readily apparent to those skilled in the art. In the interest of clarity, not all features of an actual implementation are described in this specification. It will be appreciated that in the development of any such actual implementation (as in any development project), design decisions must be made to achieve the designers' specific goals (e.g., compliance with system- and business-related constraints), and that these goals will vary from one implementation to another. It will also be appreciated that such development effort might be complex and time-consuming, but would nevertheless be a routine undertaking for those of ordinary skill in the field of the appropriate art having the benefit of this disclosure. Accordingly, the claims appended hereto are not intended to be limited by the disclosed embodiments, but are to be accorded their widest scope consistent with the principles and features disclosed herein.

Figure 1:
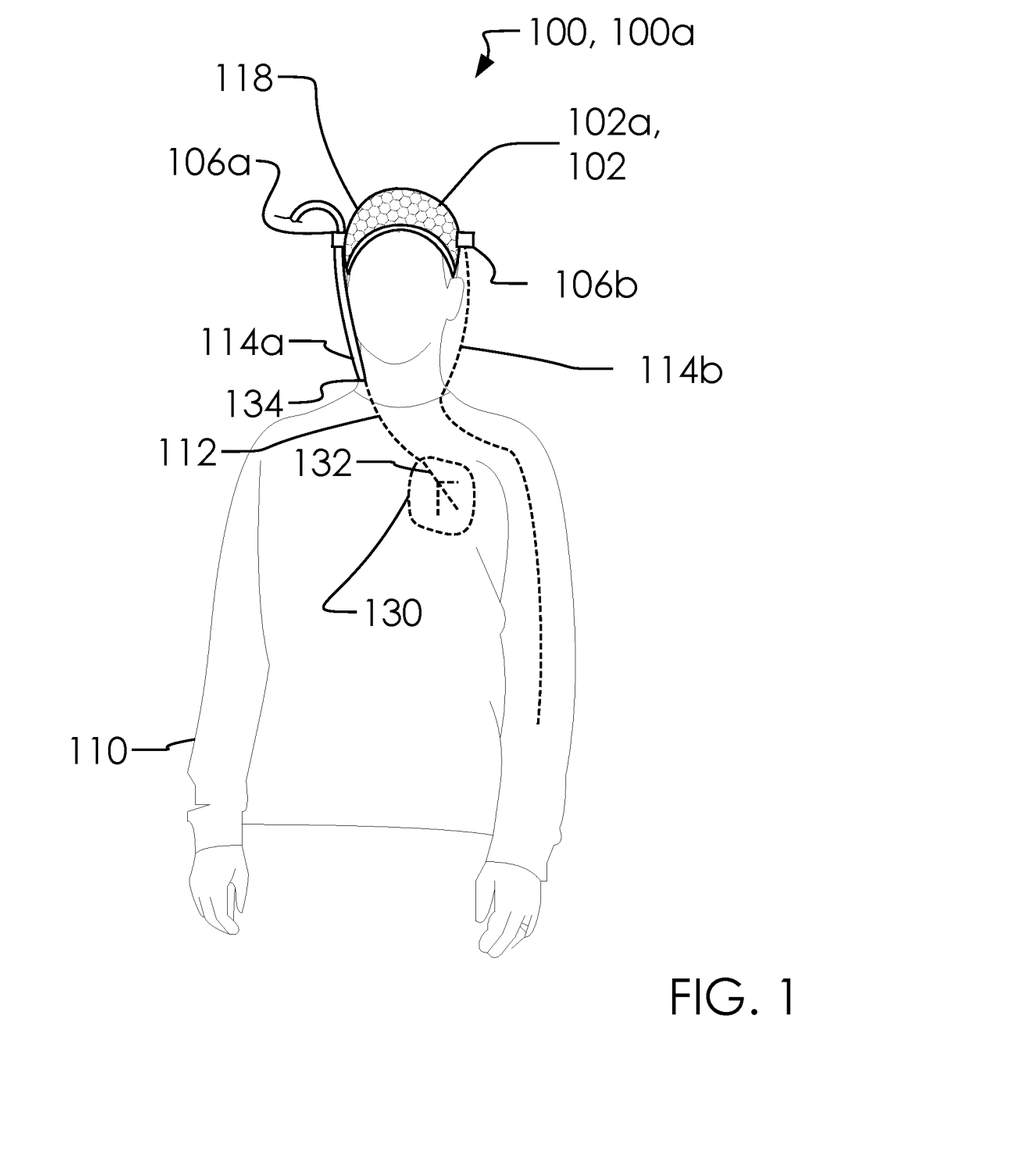

These parts are illustrated in the figures and discussed below:

a catheter holder assembly 100
a catheter holder assembly 100a
a catheter holder assembly 100b
head mount assembly 102
a first head mount assembly 102a
a second head mount assembly 102b
a one or more catheter holder 106 comprising a first catheter holder 106a and a second catheter holder 106b
a user 110
a pulmonary artery 112
a one or more catheter tubes 114 a first catheter tube 114a
a second catheter tube 114b
a head 118
a heart 130
a passages 132
a catheter 134
a chin strap 202
a chin 204
an insertion point 206
a downstream 208
an upstream 210
an IV bag 212
an IV stand 214
a one or more straps 302
a first strap 302a
a second strap 302b
a one or more fasteners 304
a first fastener 304a
a second fastener 304b
a gown 306
a one or more shoulder fasteners 308
a first shoulder fastener 308a
a second shoulder fastener 308b
a two shoulders 404
a first shoulder 404a
a second shoulder 404b
a front 420
a back 422
a first side 424
a second side 426
a vertex 428
a head aperture 500
a mesh portion 502
a woven strands 504
a one or more aperture diameters 506
a first aperture diameter 506a
a second aperture diameter 506b
a one or more sides 508
a first side 508a
a second side 508b
a rim 510
a woven strands 702
a method of use steps 800
a first method of use step 800a
a second method of use step 800b
a third method of use step 800c FIG. 1 illustrates a perspective overview view of a catheter holder assembly 100a.

In one embodiment, said catheter holder assembly 100 can comprise said catheter holder assembly 100a, said catheter holder assembly 100b and said one or more catheter holders 106.

In one embodiment, said catheter holder assembly 100a can comprise said head mount assembly 102 (which can comprise said first head mount assembly 102a and/or said second head mount assembly) and said one or more catheter holders 106.

In one embodiment, said catheter holder assembly 100b can comprise said second head mount assembly 102b and said one or more catheter holders 106.

In one embodiment, said user 110 can comprise said pulmonary artery 112, said head 118, said heart 130 and said passages 132.

In one embodiment, said one or more catheter holders 106 can comprise said first catheter holder 106a and said second catheter holder 106b.

In one embodiment, said one or more catheter tubes 114 can comprise said first catheter tube 114a and said second catheter tube 114b.

In one embodiment, said first head mounted catheter holder assembly 100a can comprise a first head mount assembly 102a and one or more catheter holders 106.

In one embodiment, said first head mount assembly 102a can comprise a snood, a hairnet or similar.

In one embodiment, said first head mount assembly 102a can attach to or fit over a head 118 of a user 110. In one embodiment, one or more catheter holders 106 can hold a portion of one or more catheter tubes 114 (which can comprise a first catheter tube 114a and a second catheter tube 114b).

As is known in the art, said one or more catheter tubes 114 can attach to a pulmonary artery 112 (or another artery or a vein of a patient) of said user 110.

In one embodiment, said first catheter tube 114a can pass through a portion of said one or more catheter holders 106; wherein, one or more catheter holders 106 can wrap around a portion of said one or more catheter tubes 114 to secure said one or more catheter tubes 114 to said first head mount assembly 102a or a second head mount assembly 102b (as described below).

In the prior art, said one or more catheter tubes 114 is often taped to said user 110 in order to prevent rubbing and dislodging from said user 110. A problem arises for users when said first catheter tube 114a is to be kept in said user 110 for an extended period of time. For example, in the present case, attaching said first catheter tube 114a to said user 110 with tape allows for the collection of germs on the tape and, ultimately, infection in the pulmonary artery 112. Likewise, the prior art does not secure said first catheter tube 114a to said user 110 for an extended period of time, as tape loses its adhesiveness over time. Further, tape may cause a restricted movement of air to said user 110's skin. For patients which have facial hair, tape may not adhere to said facial hair. Likewise, often a patient may have sensitive skin which reacts negatively to tape. FIG. 1B further illustrates a heart 130 and a one or more passages 132 within said heart 130.

In one embodiment, said user 110 may need a catheter 134. In one embodiment, said catheter 134 can comprise be used for diagnostic purposes. For example, it can detect heart failure or sepsis, monitor therapy, evaluate the effects of drugs and/or deliver drugs to the heart of a user. One advantage of said catheter 134 can be to direct, simultaneous measurement of pressures in the right atrium, right ventricle, pulmonary artery, and the filling pressure of the left atrium.

As is used in the prior art, taping said first catheter tube 114a to said user 110 in order to hold said catheter 134 in place, can lead to dislodging of and infection at said catheter 134. One advantage of said head mounted catheter holder assembly and method of use, as disclosed herein, is the avoidance of these and other maladies associated with the prior art.

In one embodiment, said catheter holder assembly 100 can protect said user 110 by isolating tugs and pulls on said catheter 134 when said one or more catheter tubes 114 is moved upstream from said user 110. In one embodiment, said catheter holder assembly 100 can be elastic allowing said first catheter tube 114a to move slightly from said head 118 but not dislodge said catheter 134 entirely. Said catheter holder assembly 100 and their methods of use, therefore, provide protection of said user 110 from harm, infection, and removal of said catheter 134 (or any catheter) while in use.

Figure 2:
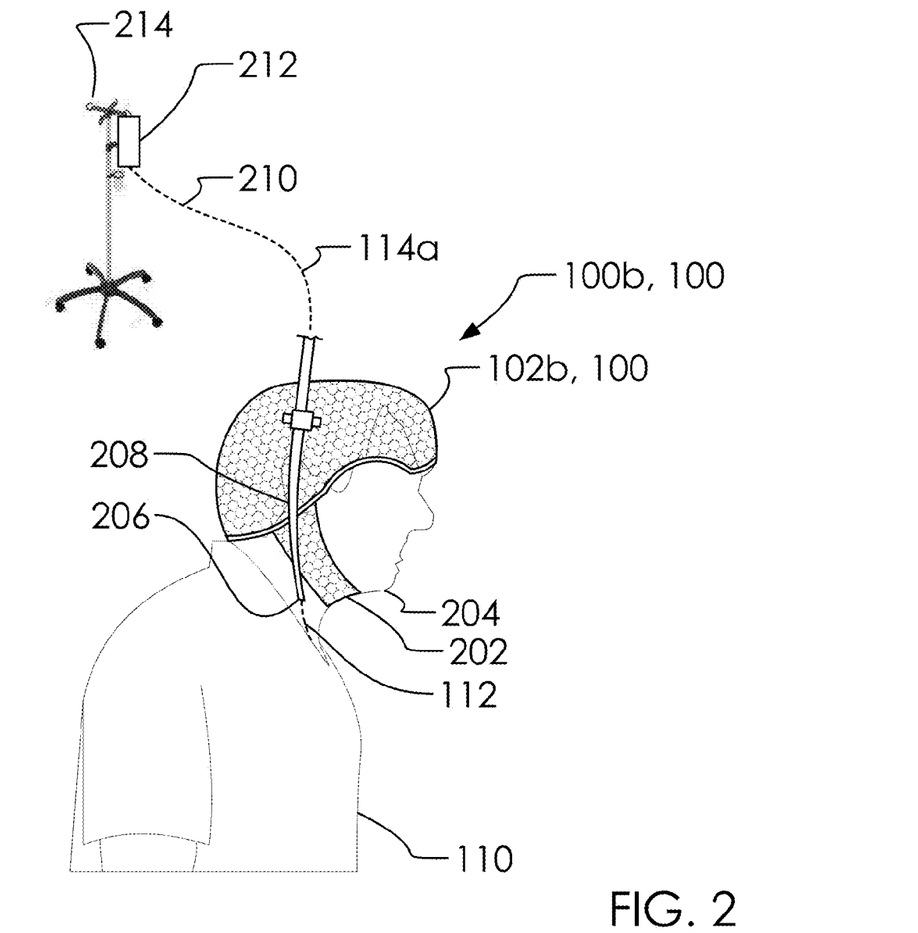
FIG. 2 illustrates a perspective overview view of a catheter holder assembly 100b.

FIG. 2 illustrates a perspective overview view of a catheter holder assembly 100b.

In one embodiment, said catheter holder assembly 100b can comprise said chin strap 202, said downstream 208 and said upstream 210.

In one embodiment, said second head mount assembly 102b can comprise said downstream 208.

Said catheter holder assembly 100b can comprise second head mount assembly 102b which can comprise chin strap 202, as illustrated.

In one embodiment, said chin strap 202 can hold said second head mount assembly 102b snuggly on said head 118 of said user 110.

In one embodiment, said chin strap 202 can be fastened by a fastener. Said fastener can comprise at least one of a hook and eye, a hook-and-loop fasteners (such as Velcro®), a button and eye, a zipper and fly, and a magnetic attraction.

In one embodiment, said catheter tube 114a can attach to said insertion point 206 at a first end and to an IV bag 212 at a second end. In one embodiment, said IV bag 212 is held by an IV stand 214. As is known in the art, movement of said user 110 can cause said catheter tube 114a to put stress on said insertion point 206. One objective of said head mounted catheter holder assembly and method of use is to decrease such stress.

In one embodiment, said second head mounted catheter holder assembly 100b can comprise a vertex strap 220, as discussed below.

In one embodiment, said one or more catheter holders 106 can isolate tugs on said upstream 210 portion of said one or more catheter tubes 114 from said downstream 208 and thereby limit harm to said insertion point 206 of said user 110.

Figure 3:
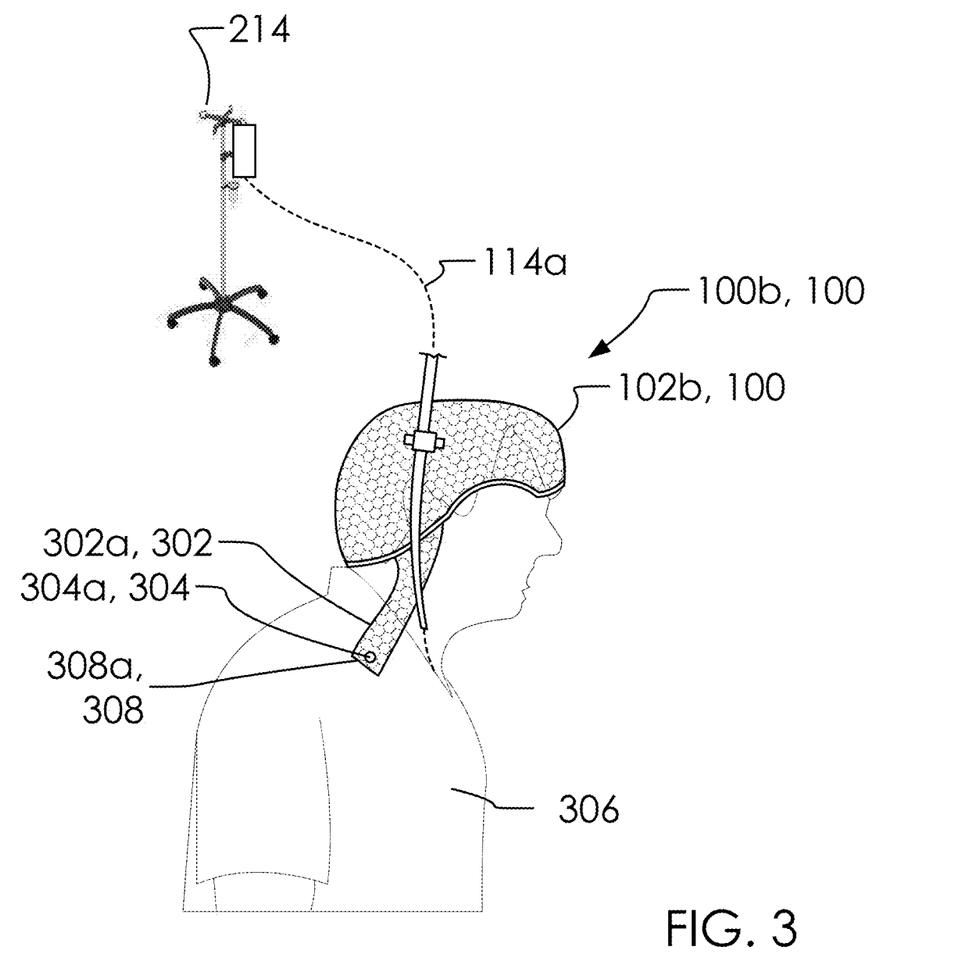
FIG. 3 illustrates a perspective overview view of a one or more straps 302.

FIG. 3 illustrates a perspective overview view of a one or more straps 302.

In one embodiment, said one or more straps 302 can comprise said first strap 302a and said second strap 302b.

In one embodiment, said one or more fasteners 304 can comprise said first fastener 304a and said second fastener 304b.

In one embodiment, said gown 306 can comprise said gown 306, said one or more shoulder fasteners 308 and said second shoulder fastener 308b.

In one embodiment, said one or more shoulder fasteners 308 can comprise said first shoulder fastener 308a and said second shoulder fastener 308b.

In one embodiment, said catheter holder assembly 100b can comprise said gown 306.

In one embodiment, said second head mount assembly 102b can comprise said one or more straps 302, said second strap 302b and said one or more fasteners 304.

In one embodiment, said one or more straps 302 can attach to said gown 306 of said user 110. Said one or more straps 302 can comprise one or more fasteners 304 and said gown 306 can comprise one or more shoulder fasteners 308. Said one or more fasteners 304 of said one or more straps 302 can selectively mate with said one or more shoulder fasteners 308 of said gown 306.

Said one or more fasteners 304 and said one or more shoulder fasteners 308 can comprise buttons, hook-and-loop fasteners, snaps, tie downs, or similar.

Removing pressure from under said chin 204 of said user 110 can remove friction and further infection and irritation.

Figure 4A:
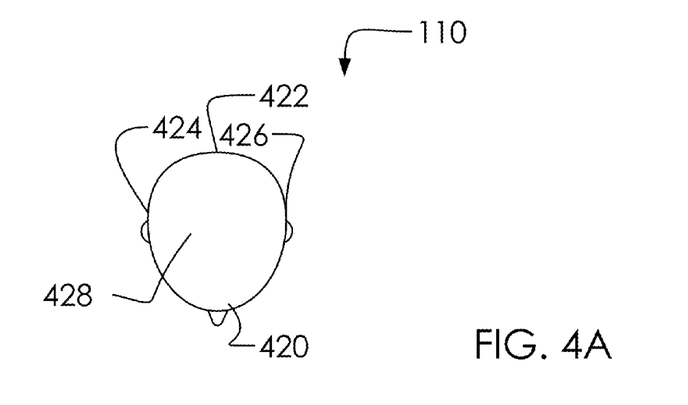
FIG. 4A illustrates an elevated top side view of a head 118.

FIG. 4A illustrates an elevated top side view of a head 118.

Figure 4B:
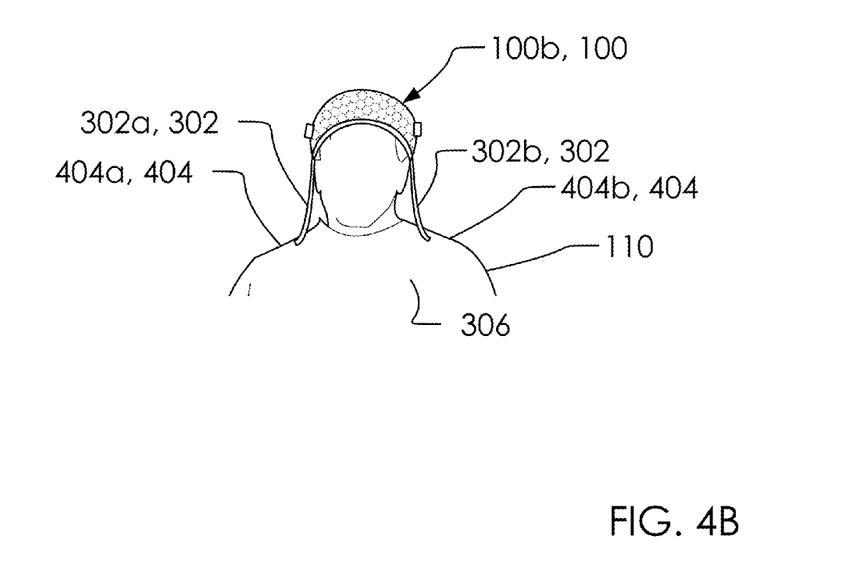
FIG. 4B illustrates a perspective overview view of a catheter holder assembly 100b.

FIG. 4B illustrates a perspective overview view of a catheter holder assembly 100b.

In one embodiment, said two shoulders 404 can comprise said first shoulder 404a and said second shoulder 404b.

In one embodiment, said head 118 can comprise said front 420, said back 422, said first side 424, said second side 426 and said vertex 428.

In one embodiment, said gown 306 can comprise said two shoulders 404.

In one embodiment, said second head mounted catheter holder assembly 100b can wrap around said head 118 of said user 110, wherein; said head 118 of said user 110 comprises a front 420, a back 422, a first side 424, a second side 426, and a vertex 428.

In one embodiment, said one or more fasteners 304 are at least one of a hook-and-loop fasteners, a hook and eye, a button and eye, a zipper and fly, and a magnetic attraction.

As would be obvious to one in the art, this configuration can be rotated and/or flipped without departing from the intended purpose and scope of this disclosure.

Figure 5A:
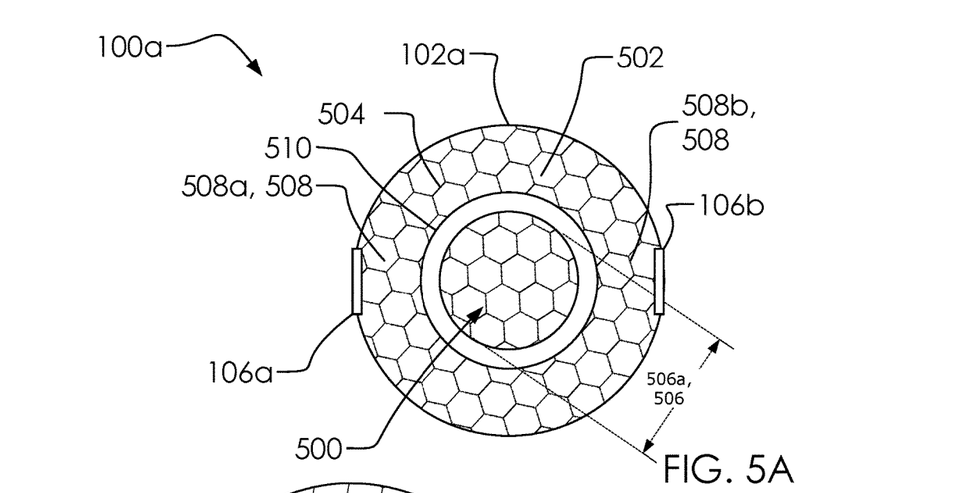

FIG. 5A illustrates an elevated bottom side view of a catheter holder assembly 100a.

Figure 5B:
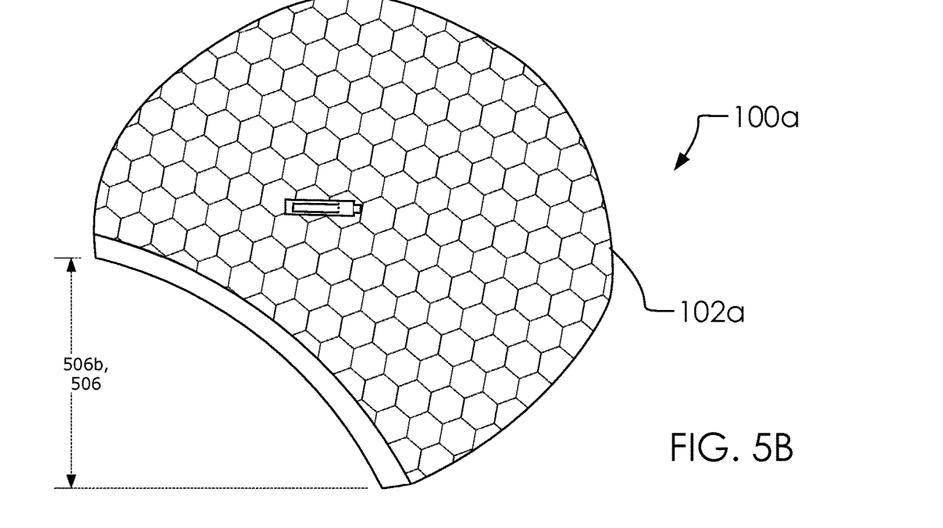

FIG. 5B illustrates an elevated first side view of a catheter holder assembly 100a.

In one embodiment, said head aperture 500 can comprise said head aperture 500 and said one or more aperture diameters 506.

In one embodiment, said one or more aperture diameters 506 can comprise said first aperture diameter 506a and said second aperture diameter 506b.

In one embodiment, said one or more sides 508 can comprise said first side 508a and said second side 508b.

In one embodiment, said catheter holder assembly 100 can comprise said head aperture 500, said second aperture diameter 506b, said one or more sides 508 and said second side 508b.

In one embodiment, said head 118 can comprise said rim 510.

In one embodiment, said first head mount assembly 102a can comprise a mesh portion 502, a fitted woven strands 504, and a one or more catheter holders.

In one embodiment, said mesh portion 502 can comprise a one of the openings between a one or more threads or cords of a net. In one embodiment, said mesh portion 502 can comprise a snood, which can comprise a type of fashionable head piece used to hold the hair of a user. As is shown in FIG. 1A, a snood can and often is used as a fashion accessory. Here, the use of the term snood, or a hair net, when discussing said mesh portion 502 of said first head mount assembly 102a can be interpreted as a device used to attach to a user's head and hold a weight such as said first catheter tube 114a. In one embodiment, said mesh portion 502 can comprise a woven netting or a one or more woven bands, as is known in the art. In one embodiment, said one or more bands can be elastic.

In one embodiment, said mesh portion 502 can comprise a solid fabric, but can also comprise of loosely knitted material (such as a yarn) or other net-like material (hereafter referred to as a netted material). In another embodiment, a small bag—netted, tatted, knitted, crocheted, or knotted—of fine thread, can enclose a bob of long hair on the back of the head or hold it close to the nape.

In one embodiment, said fitted woven strands 504 can be elastic allowing for a variable circumference and snug fit around said head 118 of said user 110. For example, in one embodiment, said mesh portion 502 is illustrated with a first aperture diameter 506a in FIG. 5A and with a second aperture diameter 506b in FIG. 5B. In another embodiment, said fitted woven strands 504 can comprise a draw string which allows for a variable circumference, as is known in the art. In one embodiment, said mesh portion 502 can be buttoned or fastened in a variety of manners as would be obvious to one in the art.

In one embodiment, said one or more catheter holders can attach to a side portions which can comprise a first side 508a and a second side 508b of said mesh portion 502 of said first head mount assembly 102a. Said one or more catheter holders of said first head mount assembly 102a can be substantially identical to those of said second head mount assembly 102b.

Figure 6:
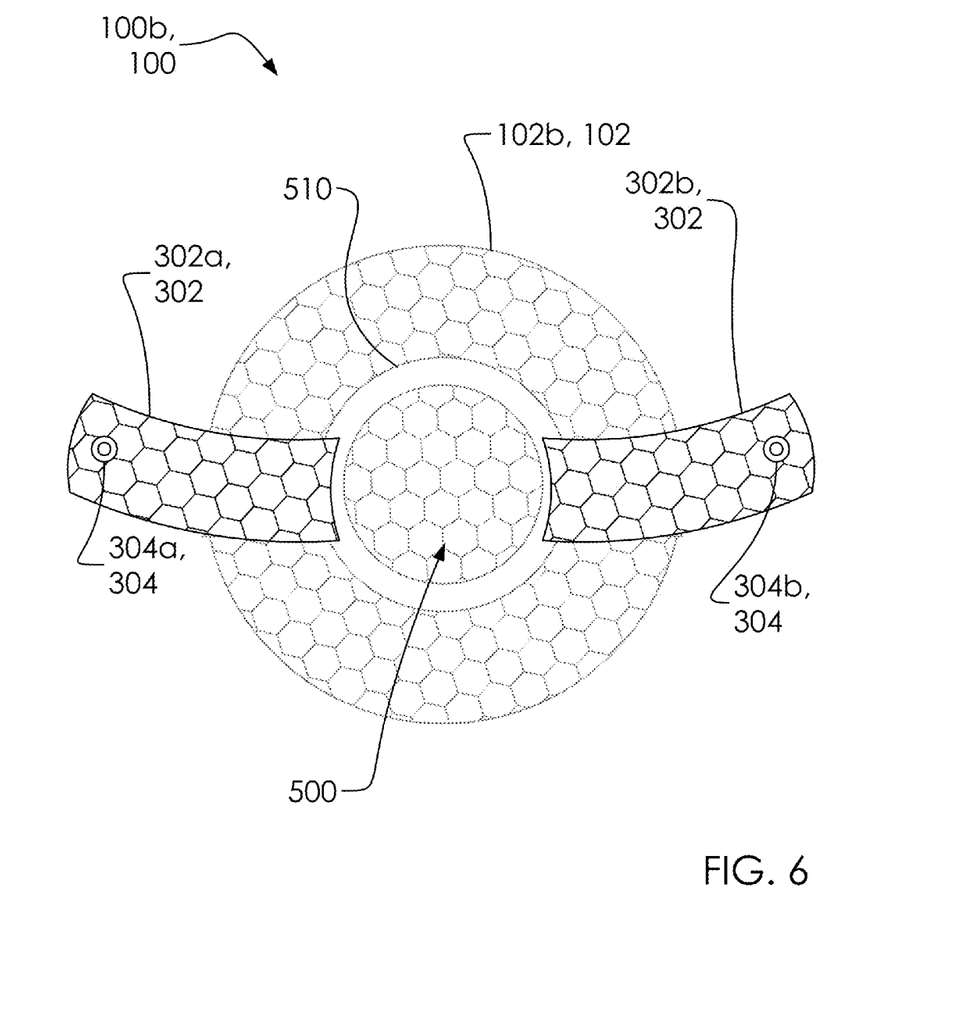
FIG. 6 illustrates an elevated bottom side view of a catheter holder assembly 100b.

FIG. 6 illustrates an elevated bottom side view of a catheter holder assembly 100b.

In one embodiment, said one or more straps 302 can attach to rim 510 and extend out from said one or more sides 508.

In one embodiment, said rim 510 can comprise an elastic material sufficient to hold said catheter holder assembly 100 on said head 118 of said user 110, as is known in the art.

In one embodiment, said one or more fasteners 304 can attach to one another rather than said gown 306, in such a case said one or more fasteners 304 can form said chin strap 202 without use of said gown 306.

Figure 7:
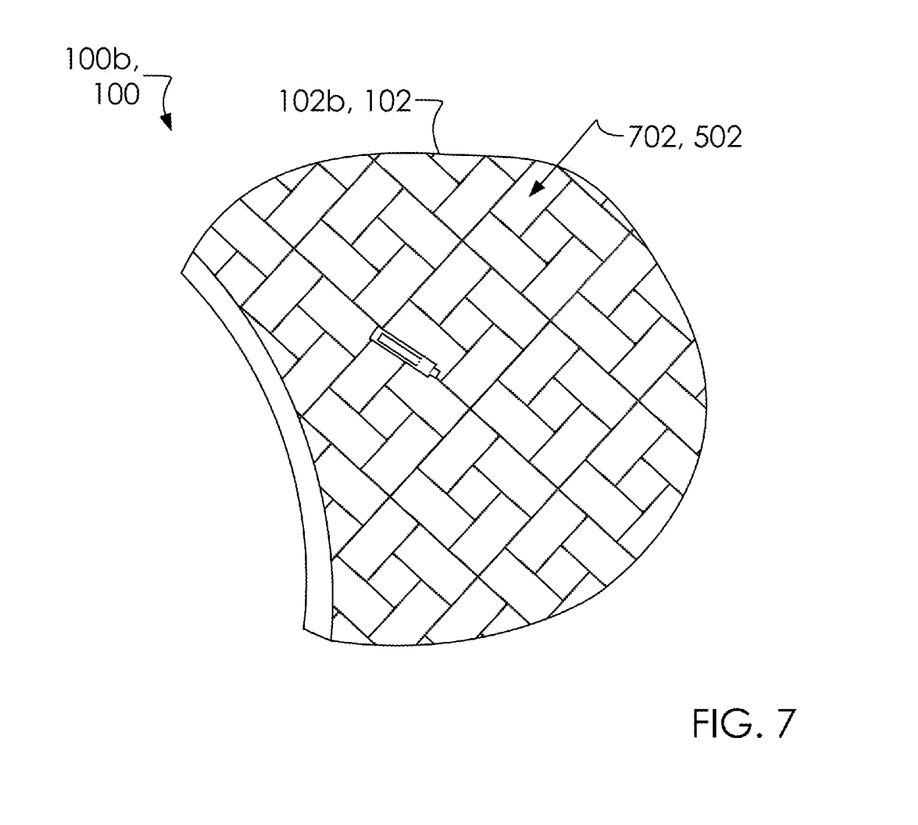
FIG. 7 illustrates an elevated first side view of a woven strands 702.

FIG. 7 illustrates an elevated first side view of a woven strands 702.

In one embodiment, said mesh portion 502 can comprise said woven strands 702 and said woven strands 702.

In one embodiment, said catheter holder assembly 100b can comprise said mesh portion 502 comprising said woven strands 702.

Figure 8:
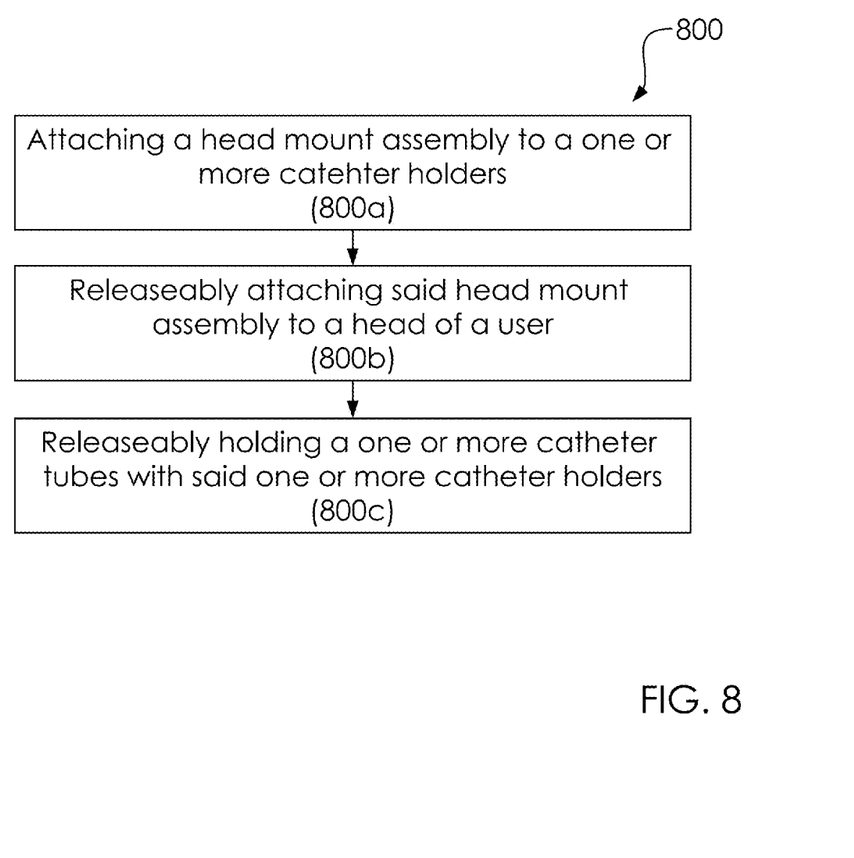
FIG. 8 illustrates a flow chart view of a method of use steps 800.

FIG. 8 illustrates a flow chart view of a method of use steps 800.

In one embodiment, said method of use steps 800 can comprise said first method of use step 800a, said second method of use step 800b, said third method of use step 800c and said third method of use step 800c.

In one embodiment, said mesh portion 502 can comprise said method of use steps 800.

In one embodiment, said method of use steps 800 can comprise a first method of use step 800a (which can comprise attaching a head mount assembly to a one or more catheter holders), a second method of use step 800b (which can comprise releaseably attaching said head mount assembly to a head of a user), and a third method of use step 800c (which can comprise releaseably holding a one or more catheter tubes with said one or more catheter holders)

The following sentences are included for completeness of this disclosure with reference to the claims.

A catheter holder assembly 100 for selectively holding a portion of a one or more catheter tubes 114 to a head 118 of a user 110. Comprising head mount assembly 102, a one or more catheter holders 106, said one or more catheter tubes 114, a catheter 134. Said one or more catheter holders 106 comprise a first catheter holder 106a. Said one or more catheter holders 106 are attached to said head mount assembly 102. head mount assembly 102 is configured to releaseably attach to said head 118 of said user 110. Said one or more catheter holders 106 releaseably hold said one or more catheter tubes 114. Said one or more catheter tubes 114 each comprise said catheter 134 at a first end being a downstream 208 of said one or more catheter holders 106 and an IV bag 212 at a second end being an upstream 210 of said one or more catheter holders 106. Said catheter 134 is configured to attach to a portion of said user 110 at an insertion point 206. Said catheter holder assembly 100 is configured to relieve stress between said catheter 134 and said user 110 by supporting one or more catheter tubes 114 between said insertion point 206 and said IV bag 212. Said one or more catheter holders 106 are positioned above said insertion point 206. head mount assembly 102 comprises a mesh portion 502 and a rim 510. Said mesh portion 502 wraps around a portion of said head 118. Said mesh portion 502 attaches around a circumference of said rim 510. head mount assembly 102 is configured to slide onto said head 118 by stretching said rim 510 around said head 118, and pressing a portion of said mesh portion 502 into a vertex 428 of said head 118. Said one or more catheter holders 106 attach to a portion of said head mount assembly 102.

head mount assembly 102 comprising said mesh portion 502 and said rim 510. Said mesh portion 502 is attached to a circumference of said rim 510. Said rim 510 comprises a head aperture 500. head mount assembly 102 is configured to selectively attach to said head 118 by stretching a portion of said rim 510 around said head 118, sliding a portion of said head 118 through said head aperture 500. Said rim 510 comprises a one or more aperture diameters 506. Said rim 510 comprises and elastic material. Said one or more aperture diameters 506 vary depending on pressure applied to said rim 510.

head mount assembly 102 comprising said mesh portion 502 and said rim 510. Said mesh portion 502 comprising a non-irritant material configured to prevent friction injuries to said head 118 of said user 110.

Said mesh portion 502 of head mount assembly 102 comprises a microfiber material configured to limit skin irritation by stretching and allowing airflow while in use.

Said mesh portion 502 of head mount assembly 102 comprises a silicon material configured to limit skin irritation.

head mount assembly 102 comprising said mesh portion 502 and said rim 510. Said mesh portion 502 comprising an elastic netting configured to allow said head 118 to freely receive airflow under head mount assembly 102.

head mount assembly 102 comprising said mesh portion 502 and said rim 510. Said mesh portion 502 comprising a mesh material configured to limit skin irritation by stretching and allowing airflow while inside of head mount assembly 102.

head mount assembly 102 comprising a one or more straps 302. Said one or more straps 302 comprising a first strap 302a and a second strap 302b. head mount assembly 102 comprising a one or more sides 508 comprising a first side 508a and a second side 508b. Said first strap 302a attached to said first side 508a. Said second strap 302b attached to said second side 508b. Said catheter holder assembly 100 further comprising a gown 306 configured to be worn by said user 110. Said gown 306 comprising a one or more shoulder fasteners 308 and a two shoulders 404. Said one or more shoulder fasteners 308 are arranged on said two shoulders 404 of said gown 306. Said one or more shoulder fasteners 308 selectively attach to a one or more fasteners 304.

A chin strap 202. Said chin strap 202 attached to said rim 510 at a one or more sides 508. Said chin strap 202 configured to selectively hold head mount assembly 102 on said head 118 of said user 110.

Said one or more catheter holders 106 comprise said first catheter holder 106a and a second catheter holder 106b. head mount assembly 102 comprises a one or more sides 508 comprising a first side 508a and a second side 508b. Said first catheter holder 106a is attached to said first side 508a and said second catheter holder 106b is attached to said second side 508b. A method of use steps 800 for a catheter holder assembly 100 comprising:

A first method of use step 800a comprising attaching head mount assembly 102 to a one or more catheter holders 106. A second method of use step 800b comprising releaseably attaching head mount assembly 102 to a head 118 of a user 110, and. A third method of use step 800c comprising releaseably holding a one or more catheter tubes 114 with said one or more catheter holders 106. Wherein. head mount assembly 102 comprising a mesh portion 502 and a rim 510. Said mesh portion 502 is attached to a circumference of said rim 510. Said rim 510 comprises a head aperture 500. head mount assembly 102 is configured to selectively attach to said head 118 by stretching a portion of said rim 510 around said head 118, sliding a portion of said head 118 through said head aperture 500. Said rim 510 comprises a one or more aperture diameters 506. Said rim 510 comprises and elastic material. Said one or more aperture diameters 506 vary depending on pressure applied to said rim 510.

Various changes in the details of the illustrated operational methods are possible without departing from the scope of the following claims. Some embodiments may combine the activities described herein as being separate steps. Similarly, one or more of the described steps may be omitted, depending upon the specific operational environment the method is being implemented in. It is to be understood that the above description is intended to be illustrative, and not restrictive. For example, the above-described embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein."

The invention claimed is:

1. A catheter holder assembly for selectively holding a portion of one or more catheter tubes to a head of a user, comprising:
   a head mount assembly, one or more catheter holders, said one or more catheter tubes, a catheter;
   said one or more catheter holders comprise a first catheter holder;
   said one or more catheter holders are attached to said head mount assembly;
   said head mount assembly is configured to releaseably attach to said head of said user;
   said one or more catheter holders releaseably hold said one or more catheter tubes;
   said one or more catheter tubes each comprise
      said catheter at a first end being a downstream of said one or more catheter holders and
      an IV bag at a second end being an upstream of said one or more catheter holders;
   said catheter is configured to attach to a portion of said user at an insertion point;
   said catheter holder assembly is configured to relieve stress between said catheter and said user by
      supporting said one or more catheter tubes between said insertion point and said IV bag;
   said one or more catheter holders are positioned above said insertion point;
   said head mount assembly comprises a mesh portion and a rim;
   said mesh portion configured to wrap around a first portion of said head;
   said mesh portion attaches around a circumference of said rim;
   said head mount assembly is configured to slide onto said head by
      stretching said rim around said head, and
      pressing a portion of said mesh portion into a vertex of said head;
   said one or more catheter holders attach to a portion of said head mount assembly;
   said one or more catheter holders comprise said first catheter holder and a second catheter holder;
   said head mount assembly comprises one or more sides comprising a first side and a second side; and
   said first catheter holder is attached to said first side and said second catheter holder is attached to said second side.

2. The catheter holder assembly from claim 1, wherein:
said rim comprises a head aperture;
said head mount assembly is configured to selectively attach to said head by
   stretching a portion of said rim around said head,
   sliding a second portion of said head through said head aperture;
said rim comprises one or more aperture diameters;
said rim comprises an elastic material; and
said one or more aperture diameters vary depending on pressure applied to said rim.

3. The catheter holder assembly from claim 1, wherein:
said mesh portion comprising a non-irritant material configured to prevent friction injuries to said head of said user.

4. The catheter holder assembly from claim 3, wherein:
said mesh portion of said head mount assembly comprises a microfiber material configured to limit skin irritation by stretching and allowing airflow while in use.

5. The catheter holder assembly from claim 3, wherein:
said mesh portion of said head mount assembly comprises a silicon material configured to limit skin irritation.

6. The catheter holder assembly from claim 1, wherein:
said mesh portion comprising an elastic netting configured to allow said head to freely receive airflow under said head mount assembly.

7. The catheter holder assembly from claim 1, wherein:
said mesh portion comprising a mesh material configured to limit skin irritation by stretching and allowing airflow while inside of said head mount assembly.

8. The catheter holder assembly from claim 1, wherein:
said head mount assembly comprising one or more straps;
said one or more straps comprising a first strap and a second strap;
said head mount assembly comprising one or more sides comprising a first side and a second side;
said first strap attached to said first side;
said second strap attached to said second side;
said catheter holder assembly further comprising a gown configured to be worn by said user;
said gown comprising one or more shoulder fasteners and two shoulders;
said one or more shoulder fasteners are arranged on said two shoulders of said gown;
said one or more straps comprise one or more fasteners; and
said one or more shoulder fasteners of said gown are configured to selectively attach to said one or more fasteners of said one or more straps.

9. The catheter holder assembly from claim 1, further comprising:

a chin strap;
said chin strap attached to said rim at one or more sides; and
said chin strap configured to selectively hold said head mount assembly on said head of said user.

10. A method of use steps for a catheter holder assembly comprising:
    selectively holding a portion of one or more catheter tubes to a head of a user with a catheter holder assembly by:
    releaseably attaching a head mount assembly to said head of said user, and;
    releaseably holding said one or more catheter tubes with said one or more catheter holders;
    wherein said catheter holder assembly comprises said head mount assembly, said one or more catheter holders, said one or more catheter tubes, a catheter;
    said one or more catheter holders are attached to said head mount assembly;
    said one or more catheter tubes each comprise
    said catheter at a first end being a downstream of said one or more catheter holders and an IV bag at a second end being an upstream of said one or more catheter holders;
    attaching said catheter to a portion of said user at an insertion point;
    said catheter holder assembly is configured to relieve stress between said catheter and said user by
    supporting said one or more catheter tubes between said insertion point and said IV bag;
    positioning said one or more catheter holders above said insertion point;
    said head mount assembly comprising a mesh portion and a rim;
    wrapping said mesh portion around a first portion of said head;
    attaching said mesh portion to a circumference of said rim;
    sliding said head mount assembly onto said head by stretching said rim around said head, and
    pressing a portion of said mesh portion into a vertex of said head;
    said one or more catheter holders comprise a first catheter holder and a second catheter holder; said head mount assembly comprises one or more sides comprising a first side and a second side; and
    said first catheter holder is attached to said first side and said second catheter holder is attached to said second side.

* * * * *